(12) United States Patent
Edwards

(10) Patent No.: US 6,296,627 B1
(45) Date of Patent: Oct. 2, 2001

(54) URINE COLLECTION SYSTEM

(76) Inventor: Richard L. Edwards, 230 S. Ridgeview Dr., Orem, UT (US) 84058

( * ) Notice: Subject to any disclaimer, the term of this patent is extended or adjusted under 35 U.S.C. 154(b) by 0 days.

(21) Appl. No.: 09/434,887

(22) Filed: Nov. 5, 1999

Related U.S. Application Data

(60) Provisional application No. 60/107,506, filed on Nov. 6, 1998.

(51) Int. Cl.[7] .................................................... A61F 5/451
(52) U.S. Cl. .................. 604/347; 604/346; 604/349; 604/350; 604/351; 604/353; 604/322; 604/323; 604/324; 604/326; 604/327; 604/331; 604/345
(58) Field of Search .................................... 604/322–324, 604/326, 327, 331, 335, 345–347, 349–351, 353

(56) References Cited

U.S. PATENT DOCUMENTS

| | | |
|---|---|---|
| 940,077 | 11/1909 | Sherman . |
| 2,476,375 | 7/1949 | Kent . |
| 3,604,424 | 9/1971 | Windom . |
| 3,721,243 | 3/1973 | Hesterman et al. . |
| 3,739,783 | 6/1973 | Broerman . |
| 4,020,843 | 5/1977 | Kanall . |
| 4,073,295 | 2/1978 | Laufbahn . |
| 4,511,358 | 4/1985 | Johnson, Jr. et al. . |
| 4,553,968 | 11/1985 | Komis . |
| 4,713,066 | 12/1987 | Komis . |
| 4,713,067 | 12/1987 | Rothberg et al. . |
| 4,820,291 | 4/1989 | Terauchi et al. . |
| 4,846,816 | 7/1989 | Manfredi . |
| 4,892,527 | 1/1990 | Zivny . |
| 4,901,375 | 2/1990 | Dahlgren . |
| 4,994,051 | 2/1991 | Walsh . |
| 5,235,705 | 8/1993 | Belisle . |
| 5,267,989 | 12/1993 | Moyet-Ortiz . |
| 5,300,052 | 4/1994 | Kubo . |
| 5,346,483 | 9/1994 | Thaxton, Sr. . |
| 5,375,265 | 12/1994 | Selzer . |
| 5,423,785 | 6/1995 | Hart . |
| 5,520,671 | 5/1996 | Bouser . |
| 5,643,236 | 7/1997 | Hadley . |
| 5,645,541 | 7/1997 | Bouser . |
| 5,741,240 | 4/1998 | Olsen . |

*Primary Examiner*—Aaron J. Lewis
*Assistant Examiner*—Michael Bogart
(74) *Attorney, Agent, or Firm*—Morriss, Bateman, O'Bryant & Compagni

(57) ABSTRACT

A urine collection system for use by a person using a float tube comprises a flexible pouch housing a urine collection reservoir in fluid communication with the person. The pouch defines first and second openings, one for receiving a tube connected to the urine collection reservoir that is coupled to the user with a condom catheter and a second for receiving a drainage valve for conveniently emptying urine from the reservoir. A unidirectional valve is associated with the tube for preventing urine from exiting the reservoir while allowing urine to freely enter the reservoir. The pouch is preferably placed outside the float tube at or above the water level so that water pressure does not affect the operation of the urine collection system.

15 Claims, 3 Drawing Sheets

URINE COLLECTION SYSTEM

This application claims benefit of Prov. No. 60/107,506 Nov. 6, 1998.

BACKGROUND OF THE INVENTION

1. Field of the Invention

The present invention relates to a urine collection system, and, more particularly, to a urine collection system for use with float tubes, chest waders and the like when fishing or engaged in other activities in which it is difficult for the user to relieve himself without removal of various gear and without compromising the environment.

2. State of the Art

The use of float tubes for those engaged in fly fishing and other fishing activities has reached a high level of popularity. A float tube is typically comprised of an inflatable circular tube about 3 to 4 feet in diameter. A shell is formed for holding the tube, and has a seat formed therein so as to be positioned in the hole in the center of the tube. The person using a float tube typically wears waders which extend up to the chest to protect his legs and lower torso from prolonged exposure to the cold water.

Typically, the fisherman sits in the seat formed in the tube so that the buoyant tube holds the user's upper torso, arms and head above the water. Fins may be worn on the user's feet to assist the user in moving the float tube to a different location by kicking. Because the arms are not needed to move or steer the float tube, the user can fish or prepare his fishing materials while casually propelling the float tube to a desired location.

One major problem encountered by users of float tubes occurs when the user needs to urinate. In such situations, it is necessary to maneuver the float tube to the nearest shoreline, a process which can take a considerable amount of time depending on the user's original distance from the shore. Upon reaching the shore, the fisherman must remove his float tube, fins, and waders and then seek the nearest restroom. Often times, fisherman either end up urinating inside their waders or urinate on the shore.

Such situations create at least four identifiable problems. First, requiring the fisherman to reach the shore, remove all his gear, and then seek a proper location to urinate significantly reduces the amount of fishing time that would otherwise be available. Second, there may be possible health risks to the user if the user repeatedly waits for extended periods of time to urinate. Third, the environment is significantly impacted where large numbers of fisherman urinate along the shores of a lake or reservoir including harmful bacterial growth in the water itself if urine reaches the water. Untreated human waste can affect other forms of life and create biological hazards. Such environmental concerns are even more important when the reservoir or lake is a source of culinary water. There is a significant risk that human waste may enter the drinking water. A fourth concern is the embarrassment that a person may feel as he paddles his float tube to the shore, knowing that other persons in the area know of his probable intent to relieve himself on the shore. The embarrassment may be even more intense if the user happens to relieve himself before being able to leave the water or remove his gear. Despite these long standing problems, this common practice continues in view of preferable alternatives.

It is well known that portable urinal devices exist, and have found general use in hospitals and other medical applications. There are numerous types of mechanisms which allow persons who are bed-ridden to relieve themselves without need for an attending nurse. One common device for men is referred to as a condom catheter. The catheter has a condom shaped receptacle for fitting over the penis. A hollow tube typically extends from the container to channel the urine into a disposable receptacle. While such mechanisms are well known in the medical art, it has generally been the belief that because urination involves gravity flow of fluid, the urine receptacle must be placed below the level of the waist. In float tube applications where the user's waist is typically below water level, the bag which receives the urine is also disposed below the water surface. The water applies pressure resulting in a compressive force to the urine disposal bag, limiting the flow of urine into the receptacle, and occasionally forcing it back towards the user. This may be especially true if the bag is disposed on the front or rear of the leg, where it is exposed to additional pressure as the user kicks to move the float tube.

In addition, if the device does not include a venting mechanism, the combination of water pressure and air pressure in the bag (if the bag is not initially deflated) or around the bag (within the waders) can be a serious problem. As the user urinates, the air around the bag remains, placing pressure on the urine in the bag. Because the bag is disposed in the waders, there is generally little room for the bag to expand before the resilient waders or air trapped therein begin to provide a compressive force. Those who have attempted to use conventional urinals with float tubes have reported that the pressure build up can cause a considerable amount of pain if the person attempts to urinate more than a small quantity.

One approach in the art to solving this problem is disclosed in U.S. Pat. No. 5,741,240 in which the urine collection reservoir is comprised of a housing having substantially rigid side walls, or sidewalls which, though flexible, are held apart by substantially rigid support structures, to prevent a compressive force from compacting a containment volume defined by the housing. In addition, a vent tube is attached to the housing to vent air in the housing as urine is received from the condom catheter. Such a system is designed to be attached at a point below the user's waist inside the waders of the user.

Each of these urine collection systems require the user to remove a substantial amount of gear before being able to empty any such collection system that has been partially or completely filled during use. Thus, there is a need for a float tube urinal which is not hampered by water pressure, which is positioned above the water surface, and which can be readily emptied without removal of any of the user's fishing gear.

SUMMARY OF THE INVENTION

It is an object of the present invention to provide a urinal system in which urine is collected in a reservoir that is positioned at or near the water level when used in conjunction with waders or a float tube.

It is another object of the present invention to provide such a system which may be conveniently worn without restricting movement of the user.

It is another object of the present invention to provide such a system which enables a urine receptacle to expand without noticeable back pressure as urine is received.

It is yet another object of the present invention to provide such a system which can be used by fisherman and the like to urinate without removing waders and without contaminating water sources with untreated human waste.

It is still another object of the present invention to provide such a system which enables the urine to be disposed of conveniently without requiring removal of gear or the condom catheter from the user.

It is yet another object of the present invention to provide such a system which is easy to manufacture.

The above and other objects of the present invention not expressly enumerated are achieved through a float tube urinal which includes a urine inflow mechanism which is typically formed by a condom catheter or other urine receptacle (e.g. urine cup for females) which is connected by an elongate flexible tube to a urine receiving mechanism. The urine receiving mechanism is preferably housed in a housing device such as a pouch that may be carried on the outside of a float tube.

The flexible housing is preferably comprised of a first panel and a second panel, each having an outer perimeter, a distal end and a proximal end. The first and second panels are secured relative to one another, as by sewing, along a substantial portion of said outer perimeters with the exception of two openings, one at each end of the housing. The housing is preferably provided with a third opening extending across a portion thereof for removal of a urine collection bag. A fastening device is preferably secured to the third opening for selective opening and closing of the third opening.

The urine collection bag is positioned within the housing and includes a first valve secured to said distal end of the bag extending at least partially through the first opening. The first valve is utilized to empty the contents of the bag by manual manipulation of the valve.

A second valve is secured to the proximal end of the bag and is configured to prevent the contents of the bag from reentering the tube connected to the user. The distal end of the tube is thus in fluid communication with and secured to the proximal end of the bag and the proximal end is in fluid communication with and secured to a urine receptacle coupling to a user.

Preferably, an attachment device is secured to the housing for securing the housing to the float tube.

In a preferred embodiment, the fastening device is positioned proximate an upper portion of the first panel to allow viewing of the quantity of urine contained within the housing.

In yet another preferred embodiment, the first opening is positioned proximate the center of the proximal ends of the first and second panels and the said second opening is positioned proximate the center of the distal ends of the first and second panels.

Preferably, the housing is comprised of a waterproof or water repellant material that is not likely to absorb water or rot from exposure to water or sunlight for prolonged periods of time. Such a material may include nylon fabric or other materials known in the art. In addition, it is preferable that the material be at least somewhat opaque to at least obscure the contents of the reservoir.

In yet another preferred embodiment, the first valve is comprised of an externally threaded tubular member and an internally threaded cap member threadedly engageable with the externally threaded tubular member. The cap member defines a longitudinally extending bore therethrough and includes a sealing member positioned within and attached to said cap member, as with a plurality of fins extending to and between the cap member and the sealing member. Rotation of the cap member relative to the tubular member in a direction that moves the sealing member into engagement with a distal end of the tubular member closes the first valve.

In still another preferred embodiment, the cap member includes an internal abutment ring or some other structure therein for engaging with an external abutment ring or some other abutment structure around or on the tubular member to prevent the cap member from being removed from the tubular member upon rotation of the cap member in a direction that disengages the sealing member from the distal end of the tubular member. This is important as actual removal of the cap member may cause the cap member to become lost defeating the purpose of protecting the environment from contamination.

In yet another preferred embodiment, the second valve is comprised of an elongate, flexible, flattened tubular member disposed within the bag. The tubular member has a first end in fluid communication with the tube and a second end that is encouraged to close when positive pressure is placed on the bag or the internal pressure of the bag exceeds the pressure within the tube.

Preferably, the tube is provided with a first lure lock connection at the distal end of the tube for removable attachment to the second valve and a second lure lock connection at the proximal end of the tube for removable attachment to the condom catheter.

The present invention also comprises a method of urine collection by a person using a float tube. The method includes the steps of attaching a substantially flexible pouch to a float tube, inserting a urine collection bag into the pouch such that a first drainage valve is accessible through the pouch; attaching a tube to a unidirectional valve of the bag such that the tube extends through the bag, attaching a second end of the tube to a condom catheter, and securing the condom catheter to the user.

When necessary, the urine collection bag can be drained by manually opening the first drainage valve. In addition, the contents of the urine collection bag can be viewed through an opening in the pouch.

BRIEF DESCRIPTION OF THE DRAWINGS

The above and other objects, features and advantages of the invention will become apparent from a consideration of the following detailed description presented in connection with the accompanying drawings in which:

FIG. 2A is a schematic illustration showing an end view of a valve member illustrated in FIG. 2 in accordance with the principles of the present invention;

FIG. 2B is a cross-section side view of the drainage valve illustrated in FIG. 2A.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
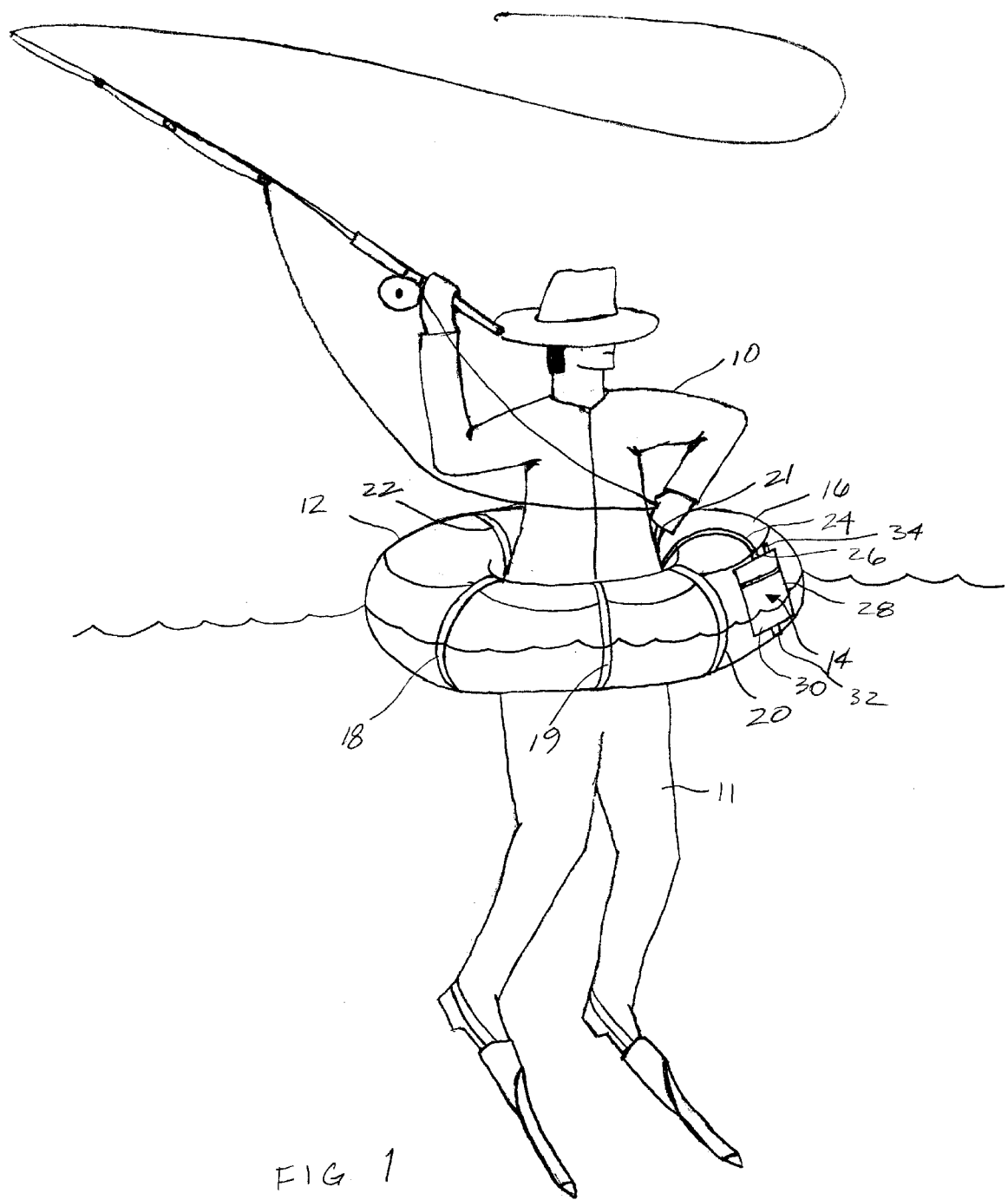
FIG. 1 is a perspective drawing of a user of a urine collection system in accordance with the present invention.

Referring to FIG. 1, there is shown a perspective view of a user 10 positioned within a float tube 12 of the type typically employed for fishing and using a urine collection system, generally indicated at 14, in accordance with the present invention. As illustrated, most float tubes 12 generally include a buoyant ring 16 typically comprised of an inflatable inner tube, of the type used for larger vehicle tires, to which the user 10 is secured with a plurality of straps 18–22. While not illustrated, it is common for the user 10 to attach various gear, such as tackle boxes, bait boxes, containers for food and/or drinks, containers or devices for retaining fish that are caught, and the like, to the float tube 12 so that the user 10 can fish on a lake for long periods of time without needing to return to shore to retrieve additional gear or for items of human consumption. Accordingly, because of the extended periods of time for which a user 10 of a float tube 12 may desire to fish and after consuming various liquids while fishing it is often the case that the user 10 needs to urinate. Because of the distance that must often be traveled in order to return to the shore and the difficultly of removing the float tube 12, waders 11 and other gear (not shown) that may be attached to the user 10 or float tube 12 once the user 10 has reached the shore, it is often very difficult and extremely uncomfortable, not to mention embarrassing, to try to quickly reach a place where one can relieve him or herself without urinating in ones clothing.

As further illustrated in FIG. 1, the urine collection system 14 includes a segment of tubing 24 connected at a first end (not shown) to and in fluid communication with the user 10 and a second end 26 connected to and in fluid communication with a urine collection receptacle 28. The urine collection receptacle 28 is provided with a flexible housing 30 or pouch for retaining a urine collection reservoir (not visible) therein. The urine collection reservoir is provided with a valve 32 for providing the user 10 the ability to selectively drain the urine collection reservoir. The housing 30 is provided with a device 34 for attaching the urine collection receptacle 28 to the float tube 12.

Figure 2:
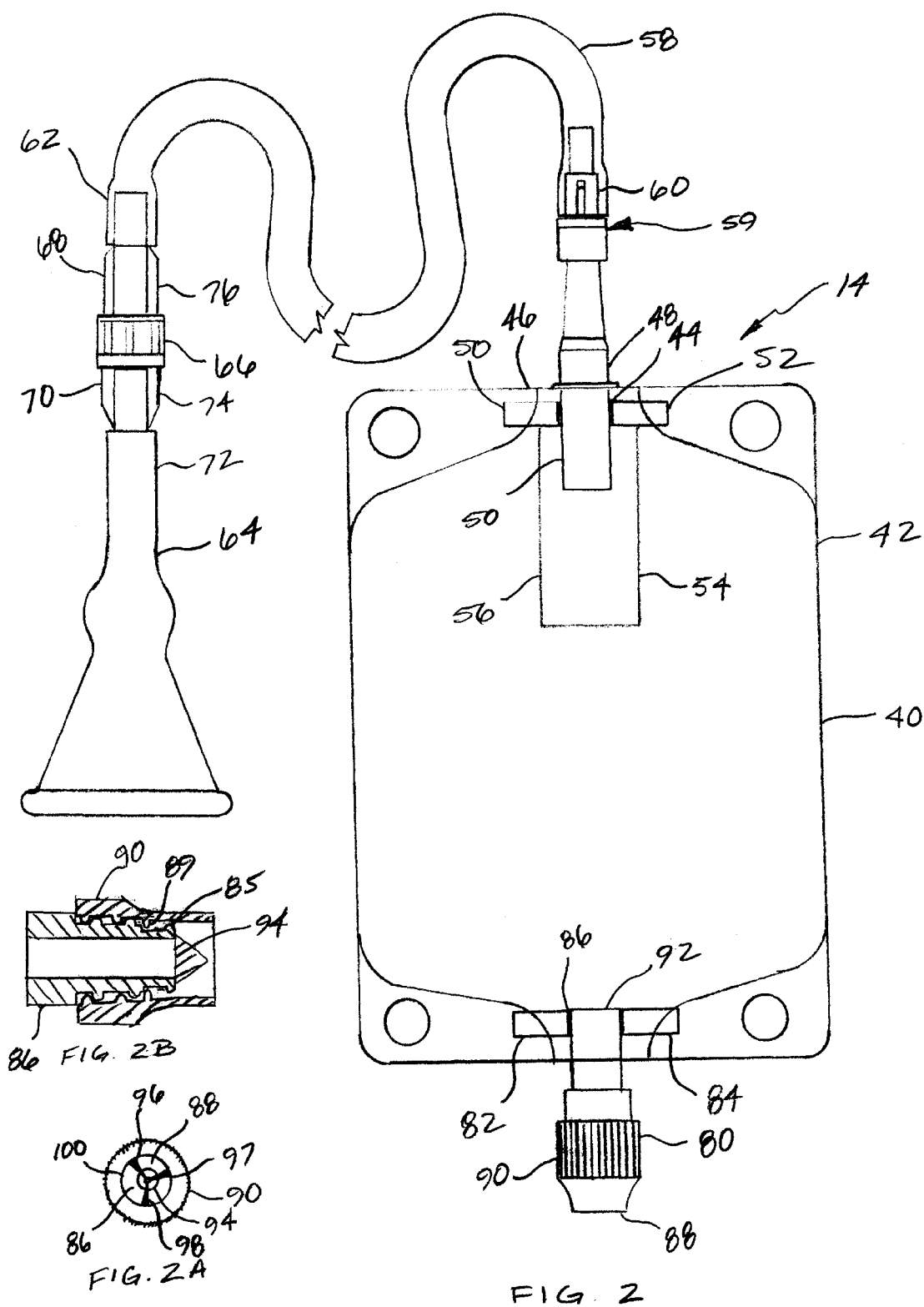
FIG. 2 is a schematic illustration showing a side view of a urine collection system in accordance with the principles of the present invention.

Referring now to FIG. 2, the urine collection system, generally indicated at 14 is comprised of a urine collection reservoir 40 preferably comprised of a flexible plastic bag 42. The bag 42 is provided with an opening 44 at a proximal end 46 to which a first tube connecting device 48 is secured. The first tube connecting device 48 may be comprised of a first tube portion 50 around which the opening 44 is secured as with plastic welds 50 and 52 which seal the bag 42 to the first tube portion 50. The bag 42 is also provided with a unidirectional or back flow valve 54 which is preferably comprised of an elongate flattened tube 56 which allows fluid to flow into the bag 42 but restricts the flow of fluid from the bag 42 into the first tube portion 50 as when a positive pressure is applied to the bag 42. The first tube portion 50 is attached to a segment of tubing 58 with a first selectively removable device, generally indicated at 59, such as a lure lock, snap lock, or other device known in the art which allows quick connection/disconnection of the tube 58 from the bag 42 while providing a fluid-tight seal while connected.

The proximal end 62 of the tube 58 is attached to a urine receptacle device 64, such as a condom catheter for males or a urine cup or catheter (not shown) for females. The urine receptacle device 64 is preferably secured to the tube 58 with a quick release locking mechanism 66 such as a lure lock mechanism, snap lock device, or other devices known in the art for providing a sealed lock that can be relatively quickly engaged and disengaged. The locking mechanism 66 illustrated in FIG. 2 is comprised of a first portion 68 attached to the tube 58 as by inserting into the proximal end 62 of the flexible tubing 58. Likewise, the locking mechanism 66 is comprised of a second portion 70 attached to the distal end 72 of the condom catheter as by insertion therein and being retained by causing the distal end 72 of the condom catheter 64 to be stretched over the second portion 70. When such locking mechanisms 66 comprise a lure lock, fins or flanges 74 and 76 may be provided for gripping the second and first portions 70 and 68, respectively, of the locking mechanism 66. As such, the condom catheter 64 can be quickly and conveniently replaced after each use of the urine collection system 14.

The bag 42 is also provided with a release valve 80 secured to and in fluid communication with the distal end of the bag 42. The valve 80 may be sealed to the bag in a similar manner as the tube portion 50 described above such as with the use of plastic welds 82 and 84, with an adhesive, or other methods known in the art. The valve 80 is preferably comprised of an elongate tube portion 86 which is secured to the bag 42 as described having external threads (not shown) on a distal end 88 thereof. A valve member 90 having internal threads (not shown) is threadedly engaged with the tube portion 86. As shown in FIG. 2A, when the valve member 90 is rotated such that the valve member 90 moves toward the proximal end 92 of the tube portion 86, a sealing member 94 abuts against the distal end 88 of the tube portion 86. The sealing member 94 is held proximate the center of the valve member 90 with fin members 96, 97, and 98 that are secured to the inside surface 100 of the valve member 90. Preferably, the threaded engagement of the valve member 90 to the tube portion 86 is such that when rotating the valve member 90 toward the distal end 88 of the tube portion 86, the valve member 90 cannot be removed from the tube portion 86 by continued rotation and thus is prevented from being removed from the tube portion 86 to further prevent the loss of the valve member 90 when rotating the valve member 90 to drain the bag 42. This feature is further illustrated in FIG. 2B in which external abutment ring 85 on the tube portion 86 will engage with internal abutment protrusion or ring 89 when the cap or valve member 90 is rotated relative to the tubular member 86 in a direction that disengages the sealing member 94 and thus prevent removal of the cap member 90 from the tubular member 86.

Figure 3:
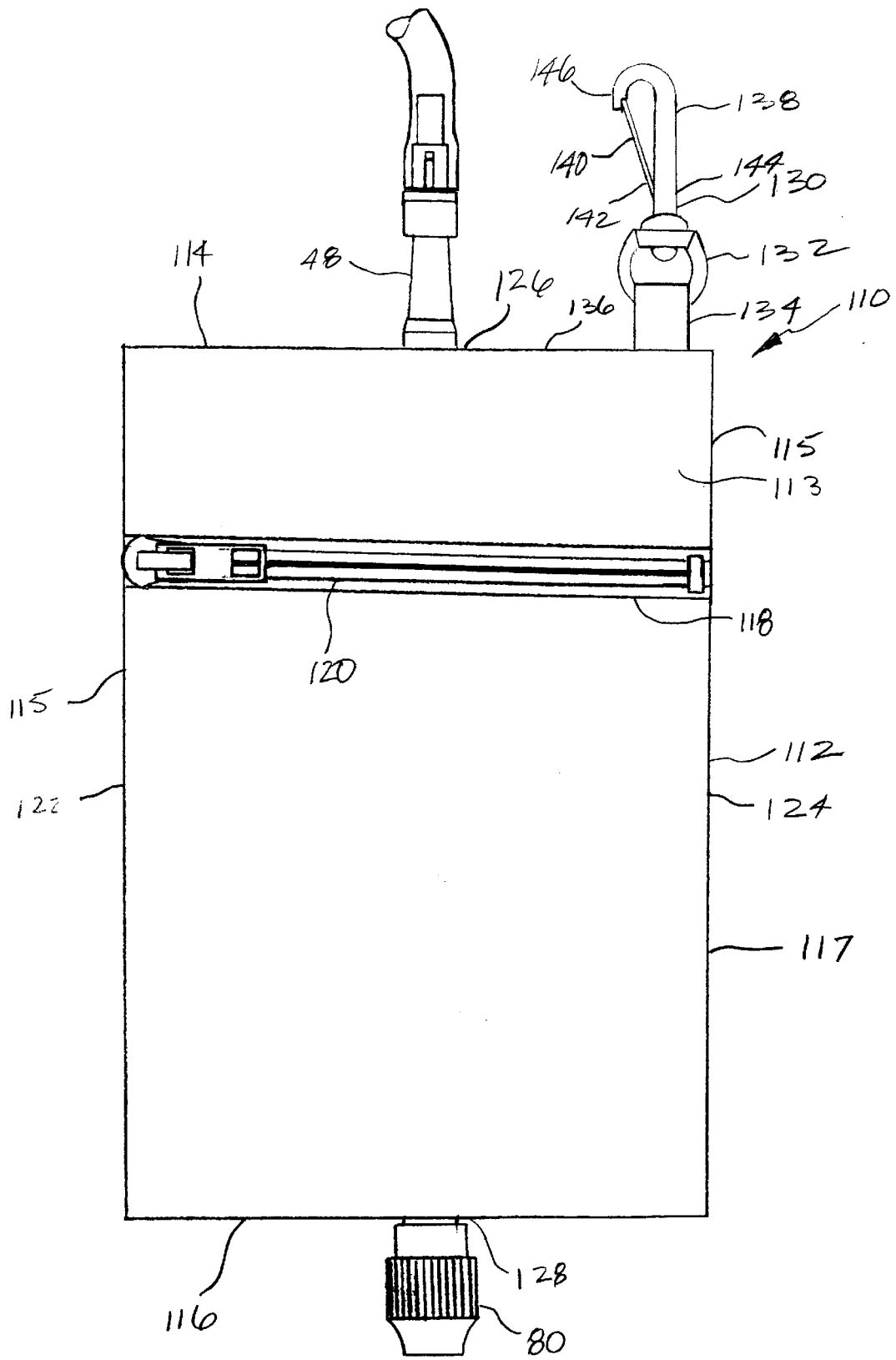
FIG. 3 is a schematic illustration showing a side view of the urine collection system of FIG. 1 in combination with a housing.

Referring now to FIG. 3, a urine collection receptacle container or housing, generally indicated at 110, in accordance with the principles of the present invention is illustrated. The housing 110 is preferably comprised of a bag or pouch 112 of generally rectangular configuration having opposing outer side walls or panels 113 and 115 preferably formed from a fabric such as a woven nylon sewn along their edges 114, 115, 116 and 117. The pouch 112 is sized to receive the bag 42 (see FIG. 2), conceal its contents and protect the bag from becoming inadvertently punctured. As will described in more detail, the pouch 112 is provided with various features to allow access to the urine collection reservoir 40. Specifically, the pouch 112 is provided with an elongate opening 118 which preferably extends from proximate the edge 115 to the edge 117 of the pouch 112. The opening 118 is further provided with a selectively openable/closeable device 120 such as a zipper as shown, a hook and loop tape faster, snaps, one or more buttons or other devices known in the art. Preferably, the opening 118 is positioned above the midpoints 122 and 124 of the edges 115 and 117, respectively, to support the reservoir 40 in a full condition even if the opening 118 has not been fastened closed, but may be positioned at any point on the pouch 112. In addition it is preferable to position the opening 118 proximate the top of the pouch 112 so that the user can look inside the opening 118 to determine the quantity of urine collected within the reservoir 40 to assess whether the reservoir 40 should be emptied. The opening 118 is provided to allow removal and or replacement of the bag 42 as desired by the user separate from the housing 110.

The pouch 112 is also provided with a first relatively small opening 126 at the edge 114 for receiving the tube connecting device 48 while retaining the bag 42 therein. Likewise, a second relatively small opening 128 is provided at the side 116 for receiving the valve 80 therethrough. Preferably, the pouch 112 is configured to substantially match the size of the bag 42 but comprised of a flexible material that will allow the pouch to outwardly expand as the bag 42 fills with urine.

Finally, a pouch attachment device 130 is secured to the pouch 112 for selectively mounting or attaching the pouch to a float tube, a user, or other gear. As illustrated, the pouch attachment device 130 is comprised of a ring portion 132 that is secured to the pouch 112 as with a loop 134 of material that may be sewn or otherwise attached to the proximal end 136 of the pouch 112. A hook portion 138 is rotatably attached to the ring portion 132. An elongate biased member 140 is secured at a first end 142 to a first end 144 of the hook portion 138 and is biased against a second end 146 of the hook portion 138. As such the hook portion 138 and member 140 can be employed to secure the pouch 112 to some other device or apparel. Of course, after understanding the present invention those skilled in the art will appreciate that other attachment devices, such as a hook and loop fastener, snaps, buttons, or straps, may be employed to attach the pouch 112 to a float tube or other structure.

Thus, there is disclosed an improved urine collection system. It is to be understood, however, that the above-described embodiments are only illustrative of the application of the principles of the present invention. Those skilled in the art will appreciate that numerous modifications may be made without departing from the scope and spirit of the present invention. Moreover, those skilled in the art will appreciate that the present invention may have numerous applications and uses in addition to those specifically discussed.

What is claimed is:

1. An apparatus for receiving and containing urine configured for use by a person using a float tube, comprising:
   a substantially flexible housing comprised of a first panel having an outer perimeter, a distal end and a proximal end, a second panel having an outer perimeter, a distal end and a proximal end, said first and second panels secured relative to one another along a substantial portion of said outer perimeters and defining a first opening at said distal ends and defining a second opening at a proximal end thereof, said first panel defining a third opening extending across a portion thereof;
   a fastening device secured to said first panel proximate said third opening configured for selective opening and closing of said third opening;
   a urine collection bag having a distal end and a proximal end positioned within said housing;
   a first valve secured to said distal end of said bag and extending at least partially through said first opening;
   a tube having a distal end and a proximal end, said distal end of said tube in fluid communication with and secured to a proximal end of said bag;
   a second valve attached to said bag and in fluid communication with said tube for substantially preventing fluid in said bag from entering said tube while allowing fluid in said tube to enter said bag;
   a urine receptacle secured to said proximal end of said tube configured to be coupling to a user for receiving urine of the user; and
   an attachment device secured to said housing for securing said housing to the gear of the user.

2. The apparatus of claim 1, wherein said fastening device is positioned proximate an upper portion of said first panel.

3. The apparatus of claim 1, wherein said first opening is positioned proximate the center of said proximal ends of said first and second panels.

4. The apparatus of claim 1, wherein said second opening is positioned proximate the center of said distal ends of said first and second panels.

5. The apparatus of claim 1, wherein said housing is comprised of an opaque nylon fabric.

6. The apparatus of claim 1, wherein said first valve is comprised of an externally threaded tubular member and an internally threaded cap member threadedly engageable with said externally threaded tubular member, said cap member defining a longitudinally extending bore therethrough and including a sealing member positioned within and attached to said cap member, whereby rotation of said cap member relative to said tubular member in a direction that moves said sealing member into engagement with a distal end of said tubular member closes said first valve.

7. The apparatus of claim 6, wherein said cap member includes an internal abutment ring positioned therein for engaging with an external abutment ring around said tubular member to prevent said cap member from being removed from said tubular member upon rotation of said cap member in a direction that disengages said sealing member from said distal end of said tubular member.

8. The apparatus of claim 1, wherein said second valve is comprised of an elongate, flexible, flattened tubular member disposed within said bag having a first end in fluid communication with said tube and a second end that encouraged to close when positive pressure is placed on the bag.

9. The apparatus of claim 1, wherein said tube is provided with a first lure lock connection at said distal end of said tube for removable attachment to said second valve and a second lure lock connection at said proximal end of said tube for removable attachment to said urine receptacle.

10. An apparatus for collecting urine of a person using a float tube, comprising:
   a pouch defining a first opening and a second opening;
   a urine collection reservoir positioned within said pouch;
   a unidirectional valve associated with said first opening, in fluid communication with said reservoir, and configured for allowing urine to enter said reservoir but substantially preventing urine from escaping from said reservoir;
   a manually operable valve extending through said second opening and in fluid communication with said reservoir for selectively allowing urine contained within said reservoir to be drained therefrom;
   a condom catheter; and
   an elongate tube having a first end and a second end, said first end connected to and in fluid communication with said unidirectional valve and said second end connected to and in fluid communication with said condom catheter.

11. The apparatus of claim 10, further including an securing device attached to said pouch for attaching said pouch to a float tube.

12. The apparatus of claim 10, wherein said manually operable valve is comprised of an externally threaded tubular member and an internally threaded cap/member threadedly engageable with said externally threaded tubular member, said cap member defining a longitudinally extending bore therethrough and including a sealing member positioned within and attached to said cap member by a plurality of fins, whereby rotation of said cap member relative to said tubular member in a direction that moves said sealing member into engagement with a distal end of said tubular member closes said first valve.

13. The apparatus of claim 12, wherein said cap member includes an internal abutment circumscribing said bore for engaging with an external abutment ring extending around said tubular member to prevent said cap member from being removed from said tubular member upon rotation of said cap member in a direction that disengages said sealing member from said distal end of said tubular member.

14. The apparatus of claim 10, wherein said unidirectional valve is comprised of an elongate, flexible, flattened tubular member disposed within said bag having a first end in fluid communication with said tube and a second end that encouraged to close when positive pressure is placed on the bag.

15. The apparatus of claim 10, wherein said tube is provided with a first lure lock connection at said distal end of said tube for removable attachment to said second valve and a second lure lock connection at said proximal end of said tube for removable attachment to said urine receptacle.

* * * * *